(12) United States Patent
Fujii et al.

(10) Patent No.: US 10,451,555 B2
(45) Date of Patent: Oct. 22, 2019

(54) SURFACE PLASMON RESONANCE FLUORESCENCE ANALYSIS DEVICE AND SURFACE PLASMON RESONANCE FLUORESCENCE ANALYSIS METHOD

(71) Applicant: KONICA MINOLTA, INC., Chiyoda-ku (JP)

(72) Inventors: Hideyuki Fujii, Saitama (JP); Tetsuya Noda, Tokyo (JP); Yukito Nakamura, Saitama (JP)

(73) Assignee: Konica Minolta, Inc., Tokyo (JP)

( * ) Notice: Subject to any disclaimer, the term of this patent is extended or adjusted under 35 U.S.C. 154(b) by 85 days.

(21) Appl. No.: 15/116,631

(22) PCT Filed: Feb. 4, 2015

(86) PCT No.: PCT/JP2015/053102
§ 371 (c)(1),
(2) Date: Aug. 4, 2016

(87) PCT Pub. No.: WO2015/119154
PCT Pub. Date: Aug. 13, 2015

(65) Prior Publication Data
US 2016/0356717 A1    Dec. 8, 2016

(30) Foreign Application Priority Data
Feb. 5, 2014  (JP) .................. 2014-020356

(51) Int. Cl.
*G01N 21/55*  (2014.01)
*G01N 21/552*  (2014.01)
(Continued)

(52) U.S. Cl.
CPC ......... *G01N 21/648* (2013.01); *G01N 21/553* (2013.01); *G01N 21/6428* (2013.01);
(Continued)

(58) Field of Classification Search
None
See application file for complete search history.

(56) References Cited

U.S. PATENT DOCUMENTS 5,852,498 A    12/1998 Youvan et al.
6,194,223 B1    2/2001 Herrmann et al.
(Continued)

FOREIGN PATENT DOCUMENTS

EP    2579023    4/2013
JP    10-307141    11/1998
(Continued)

OTHER PUBLICATIONS

Search Report dated Sep. 7, 2017 which issued in the corresponding European Patent Application No. 15747011.3.
(Continued)

*Primary Examiner* — Neil N Turk
(74) *Attorney, Agent, or Firm* — Cozen O'Connor

(57) ABSTRACT

A surface plasmon fluorescence analysis device that has a chip holder, a light source, an angle adjustment unit, a light sensor, a filter holder, an excitation light cut filter, a scattered light transmission unit, a transmission adjustment unit, and a control unit. As seen in plan view, the area occupied by the scattered light transmission unit is arranged on the excitation light cut filter or on the filter holder and is smaller than the area of a fluorescence transmission region as seen in plan view.

16 Claims, 9 Drawing Sheets

(51) Int. Cl.
  *G01N 21/64* (2006.01)
  *G01N 33/543* (2006.01)
  *G01N 21/25* (2006.01)

(52) U.S. Cl.
  CPC ..... *G01N 33/54373* (2013.01); *G01N 21/253* (2013.01); *G01N 2021/6439* (2013.01); *G01N 2021/6471* (2013.01); *G01N 2201/068* (2013.01); *G01N 2201/0612* (2013.01); *G01N 2201/0633* (2013.01)

(56) References Cited

U.S. PATENT DOCUMENTS

| | | |
|---|---|---|
| 2011/0189787 A1 | 8/2011 | Graves |
| 2011/0205392 A1 | 8/2011 | Yokoi |
| 2013/0078146 A1 | 3/2013 | Sando et al. |
| 2013/0175457 A1* | 7/2013 | Wada ................. G01N 21/648 250/459.1 |

FOREIGN PATENT DOCUMENTS

| | | |
|---|---|---|
| JP | 2012-088248 | 5/2012 |
| JP | 2012-88248 | 5/2012 |
| WO | WO 98/45687 | 10/1998 |
| WO | WO 2012/042805 | 4/2012 |

OTHER PUBLICATIONS

Office Action dated Jul. 3, 2018 which issued in the corresponding Japanese Patent Application No. 2015-561008.

* cited by examiner

SURFACE PLASMON RESONANCE FLUORESCENCE ANALYSIS DEVICE AND SURFACE PLASMON RESONANCE FLUORESCENCE ANALYSIS METHOD

RELATED APPLICATIONS

This is a U.S. National Phase Application under 35 USC 371 of International Application PCT/JP2015/053102 filed on Feb. 4, 2015.

This application claims the priority of Japanese application no. 2014-020356 filed Feb. 5, 2014, the entire content of which is hereby incorporated by reference.

TECHNICAL FIELD

The present invention relates to a surface plasmon resonance (SPR) fluorescence analysis device and a surface plasmon resonance fluorescence analysis method in which a substance to be detected (hereinafter, referred to as "detection target substance") contained in a sample is detected by utilizing surface plasmon resonance.

BACKGROUND ART

Highly-sensitive and quantitative detection of a minute amount of a detection target substance such as protein and/or DNA in laboratory tests or the like makes it possible to perform treatment while quickly determining the patient's condition. For this reason, the analysis method and analysis device which can highly-sensitively and quantitatively detect a minute amount of a detection target substance have been in demand.

Surface plasmon-field enhanced fluorescence spectroscopy (hereinafter abbreviated as "SPFS") is known as a method which can detect a detection target substance with high sensitivity (see, for example, PTLs 1 and 2).

PTLs 1 and 2 disclose an analysis method and analysis device that utilize SPFS. In the analysis method and analysis device, a sensor chip is used, which includes: a prism composed of a dielectric; a metal film formed on one surface of the prism; and a capturing body (e.g., antibody) fixed onto the metal film. When a sample containing a detection target substance is provided on the metal film, the detection target substance is captured by the capturing body (primary reaction). The captured detection target substance is then labeled by a fluorescent material (secondary reaction). In this state, when the metal film is irradiated with excitation light through the prism at an angle where SPR occurs, localized-field light can be generated on the surface of the metal film. With this localized-field light, the fluorescent material used for labeling the captured detection target substance on the metal film is selectively excited, and the fluorescence emitted from the fluorescent material is observed. In the analysis device and analysis method, the fluorescence is detected to thereby detect the presence or amount of the detection target substance.

In such an analysis method and analysis device utilizing SPFS, an excitation-light cut filter that blocks excitation light but allows fluorescence to pass through the filter is provided before a light sensor that detects the fluorescence.

CITATION LIST

Patent Literature

PTL 1
  Japanese Patent Application Laid-Open No. 10-307141

PTL 2
  WO 2012/042805

SUMMARY OF INVENTION

Technical Problem

In the analysis method and analysis device utilizing SPFS, it is necessary to set the incident angle of excitation light with respect to the metal film such that the intensity of fluorescence is maximized, in order to sufficiently improve the detection sensitivity and detection accuracy.

Regarding this point, PTL 1 discloses emitting excitation light at an incident angle at which the intensity of reflection light from the metal film is minimized (hereinafter referred to as "resonance angle"). However, the incident angle at which the intensity of fluorescence is maximized and the resonance angle are slightly different from each other, so that the analysis method and analysis device disclosed in PTL 1 have room for improvement in detection sensitivity and detection accuracy.

In the analysis method and analysis device disclosed in PTL 2, excitation light is emitted at an incident angle at which the intensity of scattering light having the same wavelength as the excitation light and generated by SPR (hereinafter referred to as "plasmon scattering light") is maximized (hereinafter referred to as "enhanced angle"). The enhanced angle is closer to the incident angle at which the intensity of fluorescence is maximized than the resonance angle is, the analysis method and analysis device disclosed in PTL 2 are more advantageous than the analysis method and analysis device disclosed in PTL 1 in terms of detection sensitivity and detection accuracy. However, in the analysis method and analysis device disclosed in PTL 2, the plasmon scattering light is also detected using the light sensor provided for detecting fluorescence, so that there arises a problem in that the excitation-light cut filter has to be completely moved from the light path of the plasmon scattering light when the enhanced angle is determined, which causes the analysis device to grow in size.

An object of the present invention is to provide a surface plasmon resonance fluorescence analysis device and a surface plasmon resonance fluorescence analysis method each capable of determining the enhanced angle at which the plasmon scattering light is maximized, without significantly moving the excitation-light cut filter from the light path of the light-reception optical system.

Solution to Problem

The inventor and et. al of this specification have found that forming a scattering-light transmitting section that allows plasmon scattering light to pass through the section at an excitation-light cut filter or a filter holder and detecting, using a light sensor, the plasmon scattering light that has passed through the scattering-light transmitting section can solve the problem mentioned above, and have thus added further consideration to complete the present invention.

To solve the above-mentioned problems, a surface plasmon resonance fluorescence analysis device according to an embodiment of the present invention is a device to which an analysis chip including a dielectric having a metal film on one surface of the dielectric is attached and in which the metal film is irradiated with excitation light through the dielectric to excite a fluorescent material for labelling a detection target substance on the metal film, and then fluorescence emitted from the fluorescent material is detected to thereby detect the presence or amount of the detection target substance, the device including: a chip holder configured to detachably hold the analysis chip; a light source configured to emit excitation light; an angle adjusting section configured to adjust an incident angle of the excitation light with respect to the metal film to irradiate the metal film with the excitation light through the dielectric at a predetermined incident angle; a light sensor configured to detect light emitted from the vicinity of a surface of the metal film, the surface facing away from the dielectric; a light-reception optical system configured to guide the light emitted from the vicinity of the metal film to the light sensor; an excitation-light cut filter disposed in the light-reception optical system and including a fluorescent transmitting region that allows fluorescence emitted from the metal film to pass through the region but blocks at least light having a certain wavelength of the excitation light; a filter holder configured to hold the excitation-light cut filter; a scattering-light transmitting section disposed at the excitation-light cut filter or the filter holder and configured to allow plasmon scattering light emitted from the metal film to pass through the section; and a transmission adjusting section configured to adjust whether to allow the plasmon scattering light to pass through via the scattering-light transmitting section, in which an area of the scattering-light transmitting section in a plan view is smaller than an area of the fluorescent transmitting region of the excitation-light cut filter in a plan view.

Moreover, to solve the above-mentioned problems, a surface plasmon resonance fluorescence analysis device according to another embodiment of the present invention is a device to which an analysis chip including a dielectric having a metal film on one surface of the dielectric is attached and in which the metal film is irradiated with excitation light through the dielectric to excite a fluorescent material for labelling a detection target substance on the metal film, and then fluorescence emitted from the fluorescent material is detected to thereby detect the presence or amount of the detection target substance, the device including: a chip holder configured to detachably hold the analysis chip; a light source configured to emit excitation light; an angle adjusting section configured to adjust an incident angle of the excitation light with respect to the metal film to irradiate the metal film with the excitation light through the dielectric at a predetermined incident angle; a light sensor configured to detect light emitted from the vicinity of a surface of the metal film, the surface facing away from the dielectric; a light-reception optical system configured to guide the light emitted from the vicinity of the metal film to the light sensor; an excitation-light cut filter disposed in the light-reception optical system and configured to allow fluorescence emitted from the metal film to pass through the filter but blocks at least light having a certain wavelength of the excitation light; and a transmission adjusting section configured to tilt the excitation-light cut filter with respect to a normal line of a surface of the metal film such that plasmon scattering light emitted from the metal film is allowed to pass through.

Furthermore, to solve the above-mentioned problems, a surface plasmon resonance fluorescence analysis method according to an embodiment of the present invention is a method in which fluorescence that is emitted by a fluorescent material for labelling a detection target substance when the fluorescent material is excited by localized-field light on a basis of surface plasmon resonance is detected to thereby detect the presence or amount of the detection target substance, the method including: disposing the detection target substance on a metal film disposed on one surface of a dielectric; determining an enhanced angle that is an incident angle at which intensity of plasmon scattering light is maximized, by detecting the intensity of the plasmon scattering light that has been emitted from the metal film and has passed through a scattering-light transmitting section while the metal film is irradiated with excitation light through the dielectric in a state where the scattering-light transmitting section formed at an excitation-light cut filter or a filter folder configured to hold the excitation-light cut filter is moved to a position where the plasmon scattering light is allowed to pass through the section, the excitation-light cut filter including a fluorescent transmitting region which allows fluorescence to pass through the region but blocks at least light having a certain wavelength of excitation light; and irradiating the metal film with the excitation light through the dielectric such that an incident angle with respect to the metal film becomes the enhanced angle and detecting the intensity of the fluorescence that has been emitted from the fluorescent material and has passed through the fluorescent transmitting region, in a state where the fluorescent transmitting region disposed at the excitation-light cut filter is moved to a position where the fluorescence is allowed to pass through the region.

Moreover, to solve the above-mentioned problems, a surface plasmon resonance fluorescence analysis method according to another embodiment of the present invention is a method in which fluorescence which is emitted by a fluorescent material for labelling a detection target substance when the fluorescent material is excited by localized-field light on a basis of surface plasmon resonance is detected to thereby detect the presence or amount of the detection target substance, the method including: disposing the detection target substance on a metal film disposed on one surface of a dielectric; determining an enhanced angle that is an incident angle at which intensity of plasmon scattering light is maximized, by detecting the intensity of the plasmon scattering light that has been emitted from the metal film and has passed through an excitation-light cut filter while the metal film is irradiated with excitation light through the dielectric in a state where the excitation-light cut filter is tilted with respect to a normal line of a surface of the metal film such that the plasmon scattering light is allowed to pass through, the excitation-light cut filter being configured to allow fluorescence to pass through the filter but blocks at least light having a certain wavelength of the excitation light; and detecting the intensity of the fluorescence that has been emitted from the fluorescent material and has passed through the excitation-light cut filter, while the metal film is irradiated with the excitation light through the dielectric such that the incident angle with respect to the metal film becomes the enhanced angle in a state where the excitation-light cut filter is disposed at such an angle that at least light having a certain wavelength of the excitation light is blocked.

Advantageous Effects of Invention

According to the present invention, during detection of a detection target substance, using SPFS, the enhanced angle at which the plasmon scattering light is maximized can be determined without significantly moving the excitation-light cut filter from the light path of the plasmon scattering light. Therefore, according to the present invention, the presence or amount of a detection target substance can be detected with high sensitivity, high accuracy and high speed. Moreover, according to the present invention, downsizing and cost reduction of the surface plasmon resonance fluorescence analysis device can be achieved.

DESCRIPTION OF EMBODIMENTS

In the following, embodiments of the present invention are described in detail with reference to the accompanying drawings.

Embodiment 1

(Configuration of SPFS Device)

First, a surface plasmon resonance fluorescence analysis device (hereinafter also referred to as "SPFS device") according to Embodiment 1 of the present invention will be described.

SPFS devices are each used in a state where an analysis chip having a dielectric and a metal film formed on one surface of the dielectric is attached to the device. When a sample containing a detection target substance is provided on the metal film, the detection target substance is captured by a capturing body. At this time, the detection target substance may or may not be labeled by a fluorescent material. When the captured detection target substance is not labeled by the fluorescent material, the captured detection target substance is then labeled by the fluorescent material. In this state, the prism having the metal film on one surface is irradiated with excitation light such that the excitation light is under the total reflection condition with respect to the prism. Thus, the interaction between the excitation light and the free electrons in the metal film (surface plasmon resonance) occurs and generates localized-field light. In general, this localized-field light is called an "enhanced electric field" or "enhanced evanescent light," and a variation in physical quantity in the vicinity of the surface of the metal film can be measured. This localized-field light selectively excites the fluorescent material labeling the detection target substance captured on the metal film, and the fluorescence emitted from the fluorescent material is observed. The SPFS device measures the light amount of fluorescence to detect the presence or amount of the detection target substance.

Figure 1:
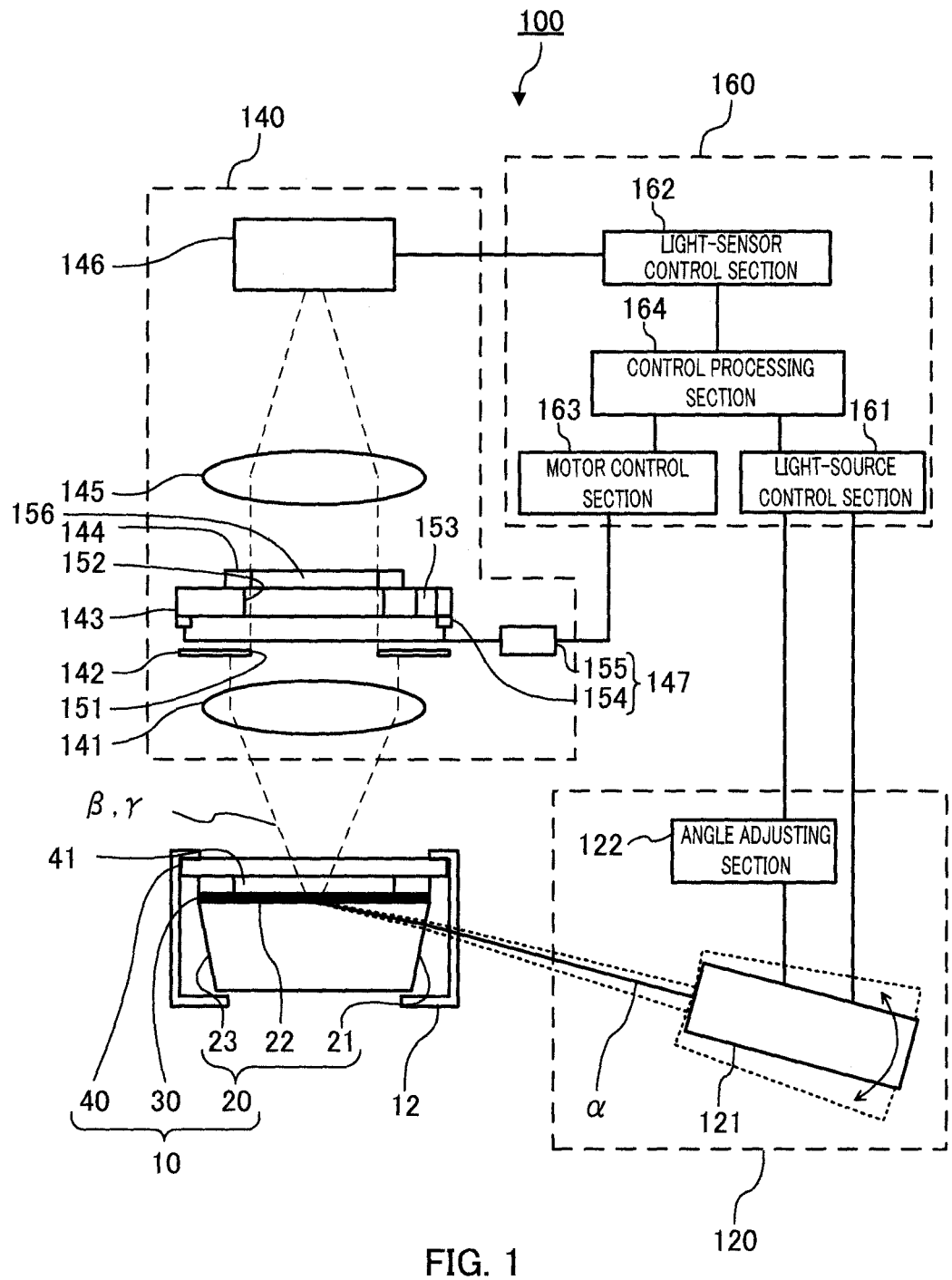
FIG. 1 is a schematic view illustrating a configuration of a surface plasmon resonance fluorescence analysis device (SPFS device) according to Embodiment 1.

FIG. 1 is a schematic view illustrating a configuration of SPFS device 100 according to Embodiment 1. As illustrated in FIG. 1, SPFS device 100 includes: chip holder 12 for detachably holding analysis chip 10; excitation optical system unit 120 for irradiating analysis chip 10 with excitation light α; light-reception optical system unit 140 for detecting the light emitted from analysis chip 10 (plasmon scattering light β and fluorescence γ); and control section 160 for controlling these components. SPFS device 100 is used in a state where analysis chip 10 is attached to chip holder 12. For this reason, analysis chip 10 is described first, and each component of SPFS device 100 is described thereafter.

As illustrated in FIG. 1, analysis chip 10 includes: dielectric 20 including incidence surface 21, film-formation surface 22 and emission surface 23; metal film 30 formed on film-formation surface 22; and channel closure 40 disposed on film-formation surface 22 or metal film 30. Normally, analysis chip 10 is replaced for each analysis.

Dielectric 20 is a transparent member that allows excitation light α to pass therethrough (prism). Dielectric 20 includes incidence surface 21, film-formation surface 22 and emission surface 23. Incidence surface 21 allows excitation light α from excitation optical system unit 120 to enter dielectric 20. Metal film 30 is formed on film-formation surface 22. Excitation light α having entered dielectric 20 is reflected by metal film 30. To be more specific, the excitation light α having entered dielectric 20 is reflected by the interface (film-formation surface 22) between dielectric 20 and metal film 30. Emission surface 23 allows excitation light α reflected by metal film 30 to be emitted outside of dielectric 20. The shape of dielectric 20 is not limited to any particular shape. In the present embodiment, the shape of dielectric 20 is a columnar shape having a trapezoidal bottom. The surface corresponding to one bottom side of the trapezoid is film-formation surface 22. The surface corresponding to one leg is incidence surface 21, and the surface corresponding to the other leg is emission surface 23. Preferably, the trapezoid serving as the bottom surface is an isosceles trapezoid. In such a configuration, incidence surface 21 and emission surface 23 are symmetrical, and the S-wave component of excitation light α does not easily remain in dielectric 20. Incidence surface 21 is formed such that excitation light α does not return to excitation optical system unit 120. This is because, when excitation light α returns to the laser diode serving as the excitation light source, the excitation state of the laser diode is disturbed, causing the wavelength and the output of the excitation light α to vary. Therefore, the angle of incidence surface 21 is set within a scanning range around the ideal enhanced angle such that excitation light α does not perpendicularly enter incidence surface 21. For example, the angle between incidence surface 21 and film-formation surface 22, and the angle between film-formation surface 22 and emission surface 23 are approximately 80 degrees. Examples of the material of dielectric 20 include a resin and glass. Preferably, the material of dielectric 20 is a resin having a refractive index of 1.4 to 1.6 and exhibiting a small birefringence.

Metal film 30 is formed on film-formation surface 22 of dielectric 20. When metal film 30 is provided, interaction (surface plasmon resonance; SPR) occurs between the photons of excitation light α which has entered film-formation surface 22 under the total reflection condition and the free electrons in metal film 30, and thus localized-field light can be generated on the surface of metal film 30. The material of metal film 30 is not limited in particular as long as the material is a metal that causes surface plasmon resonance. Examples of the material of metal film 30 include gold, silver, copper, aluminum, and their alloys. In the present embodiment, metal film 30 is a metal film.

The formation method for metal film 30 is not limited to any particular method. Examples of the formation method for metal film 30 include sputtering, vapor-deposition, and plating. Preferably, the thickness of metal film 30 is within a range from 30 nm to 70 nm, but is not limited in particular.

Moreover, although no illustration is given in particular, a capturing body for capturing a detection target substance may be fixed to a surface of metal film 30 that faces away from dielectric 20. Fixing the capturing body enables selectively detecting a detection target substance. In this embodiment, the capturing body is uniformly fixed in a predetermined region on metal film 30. The capturing body is not limited to any particular type as long as the capturing body is capable of capturing the detection target substance. For example, the capturing body may be an antibody specific to the detection target substance or a fragment of the antibody.

Channel closure 40 is disposed on the surface of metal film 30 that faces away from dielectric 20 with channel 41 interposed therebetween. When metal film 30 is only partly formed on film-formation surface 22 of dielectric 20, channel closure 40 may be disposed on film-formation surface 22 with channel 41 interposed therebetween. Together with metal film 30 (and dielectric 20), channel closure 40 forms channel 41 through which liquid such as a sample, fluorescent labeling solution, or washing solution flows. The capturing body is exposed to the inside of channel 41. Both ends of flow channel 41 are respectively connected to the inlet and outlet (both omitted in the drawing) formed on the top surface of channel closure 40. When liquid is injected into channel 41, the liquid makes contact with the capturing body in channel 41. Channel closure 40 is composed of a material that allows the light emitted from the surface of metal film 30 that faces away from dielectric 20 and emitted from the vicinity of this surface of metal film 30 (plasmon scattering light β and fluorescence γ) to pass through. Examples of the material of channel closure 40 include a resin. As long as channel closure 40 can guide the above-mentioned light to light-reception optical system unit 140, channel closure 40 may be partly composed of an opaque material. Channel closure 40 is joined to metal film 30 or dielectric 20 by bonding using a double-sided tape or an adhesive agent, laser welding, ultrasound welding, or pressure fixing using a clamping member, for example.

As illustrated in FIG. 1, excitation light α guided to dielectric 20 enters dielectric 20 from incidence surface 21. The excitation light α having entered dielectric 20 is incident on the interface (film-formation surface 22) between dielectric 20 and metal film 30 at a total reflection angle (at an angle that causes surface plasmon resonance). The reflection light from the interface is emitted to outside of dielectric 20 from emission surface 23 (not illustrated in the drawing). Meanwhile, when excitation light α is incident on the interface at an angle which causes surface plasmon resonance, plasmon scattering light β and/or fluorescence γ is emitted from metal film 30 and the vicinity of metal film 30 in the direction toward light-reception optical system unit 140.

Next, the components of SPFS device 100 are described. As described above, SPFS device 100 includes chip holder 12, excitation optical system unit 120, light-reception optical system unit 140 and control section 160.

Chip holder 12 holds analysis chip 10 at a predetermined position. Analysis chip 10 is irradiated with excitation light α from excitation optical system unit 120 in the state where analysis chip 10 is held by chip holder 12. At this time, plasmon scattering light β having the same wavelength as excitation light α and/or fluorescence γ output from the fluorescent material and/or the like is emitted upward from the surface of metal film 30 that faces away from dielectric 20 and emitted from the vicinity of the surface. In addition, excitation light α is reflected by the interface between dielectric 20 and metal film 30 and then emitted to the outside of dielectric 20 (illustration is omitted).

Excitation optical system unit 120 includes light source unit 121 that emits excitation light α, and angle adjusting section 122 that adjusts the incident angle of excitation light α with respect to the interface (film-formation surface 22) between dielectric 20 and metal film 30.

Light source unit 121 includes a laser diode (hereinafter abbreviated as "LD") as an excitation light source, and emits excitation light α (single mode laser light) toward incidence surface 21 of analysis chip 10 held by chip holder 12. To be more specific, light source unit 121 emits only a P-wave with respect to the interface such that the angle of excitation light α with respect to the interface (film-formation surface 22) between dielectric 20 and metal film 30 of analysis chip 10 is a total reflection angle. For example, light source unit 121 includes an LD unit, a waveform shaper and a shaping optical system (illustrations are omitted).

The LD unit emits collimated excitation light α having a constant wavelength and light amount such that the irradiation spot on the interface (film-formation surface 22) between dielectric 20 and metal film 30 forms a substantially circular shape. The LD unit includes: an LD as an excitation light source; a collimator that collimates excitation light α emitted from the LD; and a temperature adjusting circuit that adjusts the light amount of excitation light α to be constant. The excitation light α emitted from the LD has a flat outline shape even after the collimation. For this reason, the LD is held at a predetermined orientation, or a slit having a predetermined shape is inserted to a shaping optical system to be described hereinafter, such that the irradiation spot on the interface (film-formation surface 22) forms a substantially circular shape. In addition, the wavelength and light amount of excitation light α emitted from the LD vary depending on the temperature. For this reason, the temperature adjusting circuit monitors the light amount of the light diverged from the collimated excitation light α, using a photodiode and/or the like and adjusts the temperature of the LD, using a heater, a Peltier device and/or the like, such that the wavelength and light amount of the excitation light α are adjusted to be constant.

The waveform shaper includes a bandpass filter (hereinafter abbreviated as "BPF") and a linear polarization filter (hereinafter abbreviated as "LP") and shapes the waveform of excitation light α emitted from the LD unit. The excitation light α from the LD unit has a slight wavelength distribution width, so that the BPF changes the excitation light α from the LD unit to narrowband light composed only of a center wavelength. In addition, since the excitation light α from the LD unit is not complete linear polarization, the LP changes the excitation light α from the LD unit to complete linear polarization light. The waveform shaper may include a half-wavelength plate that adjusts the polarization direction of excitation light α such that the P-wave component is incident on metal film 30.

The shaping optical system adjusts the beam diameter, the outline shape, and/or the like of excitation light α such that the irradiation spot on the interface (film-formation surface 22) between dielectric 20 and metal film 30 has a circular shape of a predetermined size. The excitation light α emitted from the shaping optical system is emitted to dielectric 20 of analysis chip 10. The shaping optical system is a slit, a zooming section, or the like, for example.

Note that, the light source included in light source unit 121 is not limited to any particular type and may not be an LD. Examples of the light source include a light-emitting diode, a mercury lamp, and other laser light sources. In the case where the light emitted from the light source is not a beam, the light emitted from the light source is converted to a beam by a lens, mirror, slit and/or the like. In addition, in the case where the light emitted from the light source is not monochromatic light, the light emitted from the light source is converted to monochromatic light by a diffraction grating and/or the like. Moreover, when the light emitted from the light source is not linear polarization, the light emitted from the light source is converted to linear polarization light by a polarizer or the like.

Angle adjusting section 122 adjusts the incident angle of excitation light α to metal film 30 (the interface (film-formation surface 22) between dielectric 20 and metal film 30). Angle adjusting section 122 relatively turns the optical axis of excitation light α, and chip holder 12 to emit excitation light α to a predetermined position of metal film 30 (film-formation surface 22) through dielectric 20 at a predetermined incident angle. In the present embodiment, angle adjusting section 122 turns light source unit 121 about the axis orthogonal to the optical axis of excitation light α. At this time, the position of the turn axis is set such that the irradiation position on metal film 30 (film-formation surface 22) hardly moves when the incident angle is scanned. For example, when the position of the turning center is set at a position near the intersection of the optical axes of two rays of excitation light α at both ends of the scanning range of the incident angle (at a position between the irradiation position on film-formation surface 22 and incidence surface 21), the shifting of the irradiation position can be minimized.

Light-reception optical system unit (light-reception optical system) 140 is disposed to face the surface of metal film 30 that faces away from dielectric 20 in analysis chip 10 held by chip holder 12. Light-reception optical system unit 140 detects the light emitted from metal film 30 (plasmon scattering light β or fluorescence γ). Light-reception optical system unit 140 includes first lens 141, diaphragm 142, filter holder 143, excitation-light cut filter 144, second lens 145, light sensor 146, and transmission adjusting section 147. First lens 141, diaphragm 142, filter holder 143, excitation-light cut filter 144, second lens 145, and light sensor 146 are disposed opposite to the surface of metal film 30 in this order from the side of metal film 30.

First and second lenses 141 and 145 constitute a conjugate optical system that is not easily affected by stray light. The light rays that travel between first and second lenses 141 and 145 become substantially parallel light. First and second lenses 141 and 145 cause fluorescence γ emitted from metal film 30 to form an image on the light reception surface of light sensor 146.

Diaphragm 142 is disposed between first lens 141 and filter folder 143. Diaphragm 142 allows at least some of the light that has been collimated by first lens 141 (plasmon scattering light β and/or fluorescence γ) to pass through via diaphragm hole 151. The light that has passed through diaphragm 142 reaches fluorescent transmitting region 156 of excitation-light cut filter 144. The term "fluorescent transmitting region" used herein means a partial region of excitation-light cut filter 144 through which fluorescence γ controlled by diaphragm 142 (or first through-hole 152) passes during detection of fluorescence γ. The plan-view shape of diaphragm hole 151 is not limited to any particular shape. The plan-view shape of fluorescent transmitting region 156 is the same as that of diaphragm hole 151 of diaphragm 142.

Filter holder 143 holds excitation-light cut filter 144 and is disposed between diaphragm 142 and second lens 145. The shape of filter holder 143 is not limited to any particular shape as long as filter holder 143 can hold excitation-light cut filter 144. The shape of filter holder 143 may be a shape to hold excitation-light cut filter 144 from below or a shape to grip an outer edge portion of excitation-light cut filter 144, for example. In this embodiment, filter holder 143 is formed larger in size than excitation-light cut filter 144 and holds excitation-light cut filter 144 from below.

Filter holder 143 includes first through-hole 152 and second through-hole 153. First through-hole 152 is disposed at a center portion of filter holder 143. In this embodiment, first through-hole 152 is formed larger in size than diaphragm hole 151 of diaphragm 142. First through-hole 152 allows the light that has been focused by diaphragm 142 (plasmon scattering light β and/or fluorescence γ) to pass through. The light that has passed through first through-hole 152 reaches the rear surface of excitation-light cut filter 144. Second through-hole 153 is formed at filter holder 143 so as to avoid excitation-light cut filter 144 (see FIG. 1). Although details will be given hereinafter, second through-hole 153 is formed at a position distant from an end portion of fluorescent transmitting region 156, which is shorter than the diameter of fluorescent transmitting region 156. Second through-hole 153 serves as a scattering-light transmitting section that allows plasmon scattering light β to pass through and is used for determining an enhanced angle to be described hereinafter. The light that has passed through second through-hole (scattering-light transmitting section) 153 reaches light sensor 146 through second lens 145. Note that, when scattering-light transmitting section 153 allows plasmon scattering light β to pass through, scattering-light transmitting section 153 may also allow fluorescence γ to pass through. The area of scattering-light transmitting section 153 when viewed in a plan view is not limited to any particular area, but it is preferable that the area of scattering-light transmitting section 153 be not greater than $1/1000$ of the area of fluorescent transmitting region 156 when viewed in a plan view. The expression "when viewed in a plan view" used herein means a view from metal film 30.

Excitation-light cut filter 144 is disposed between diaphragm 142 and second lens 145. Excitation-light cut filter 144 includes fluorescent transmitting region 156. Fluorescent transmitting region 156 allows the fluorescence emitted from metal film 30 to pass through but blocks at least light of a certain wavelength of the excitation light. Excitation-light cut filter 144 prevents light other than the light having a wavelength of fluorescence γ from reaching light sensor 146 by reflecting or absorbing the light having a wavelength of excitation light α (plasmon scattering light β while allowing fluorescence γ to pass through the filter. More specifically, excitation-light cut filter 144 removes a noise component from the light that reaches light sensor 146, thereby making a contribution to improving the detection accuracy and sensitivity of weak fluorescence γ.

Excitation-light cut filter 144 guides only a fluorescent component to light sensor 146 and removes an excitation light component (plasmon scattering light β in order to detect the fluorescent component with a high S/N ratio. Examples of excitation-light cut filter 144 include an excitation-light reflection filter, a short-wavelength cut filter, and a bandpass filter. Excitation-light cut filter 144 is a filter composed of a multilayer film for reflecting a predetermined light component for removal, but may be a color glass filter for absorbing a predetermined light component for removal in general.

Light sensor 146 detects fluorescence γ emitted from metal film 30 or plasmon scattering light β. For example, light sensor 146 is a photomultiplier tube having a high sensitivity and a high S/N ratio. Light sensor 146 may be an avalanche photodiode (APD) or the like. Note that, the size of the irradiation spot of excitation light α on one surface of metal film 30 (the surface facing away from dielectric 20) is adjusted to a size smaller than the size of the measurement region of light sensor 146 on the other surface of metal film 30 (the surface facing away from first lens 141). This configuration makes it possible to prevent the irradiation spot from being out of the measurement region even when the irradiation spot is slightly shifted in position due to an error of each parameter of dielectric 20.

Transmission adjusting section 147 moves scattering-light transmitting section 153 on a light path in light-reception optical system unit 140 when light sensor 146 detects plasmon scattering light β. Meanwhile, transmission adjusting section 147 moves fluorescent transmitting region 156 within the light path of light-reception optical system unit 140 and also moves scattering-light transmitting section 153 to outside of the light path within light-reception optical system unit 140 when light sensor 146 detects fluorescence γ. Transmission adjusting section 147 includes: stage 154 that supports filter folder 143; and motor 155 that serves as a driving source for moving filter holder 143 (scattering-light transmitting section 153) via stage 154. Although details will be given hereinafter, transmission adjusting section 147 is capable of determining an enhanced angle by moving scattering-light transmitting section 153 within or outside the light path of light-reception optical system unit 140 without significantly moving filter folder 143 and excitation-light cut filter 144.

Control section 160 integrally controls driving sections and makes quantification of the light reception amount of light sensor 146. In this embodiment, control section 160 includes: light-source control section 161 that controls light source unit 121; light-sensor control section 162 that controls light sensor 146; motor control section 163 that controls motor 155; and control processing section 164. Control processing section 164 comprehensively controls light-source control section 161, light-sensor control section 162, and motor control section 163 so as to control the entire operation of SPFS device 100. Control section 160 is a computer for executing software, for example. As described hereinafter, control section 160 (control processing section 164) controls the incident angle of excitation light α with respect to metal film 30 (film-formation surface 22) during fluorescence measurement on the basis of the measurement result of plasmon scattering light β obtained by light sensor 146.

Figure 2:
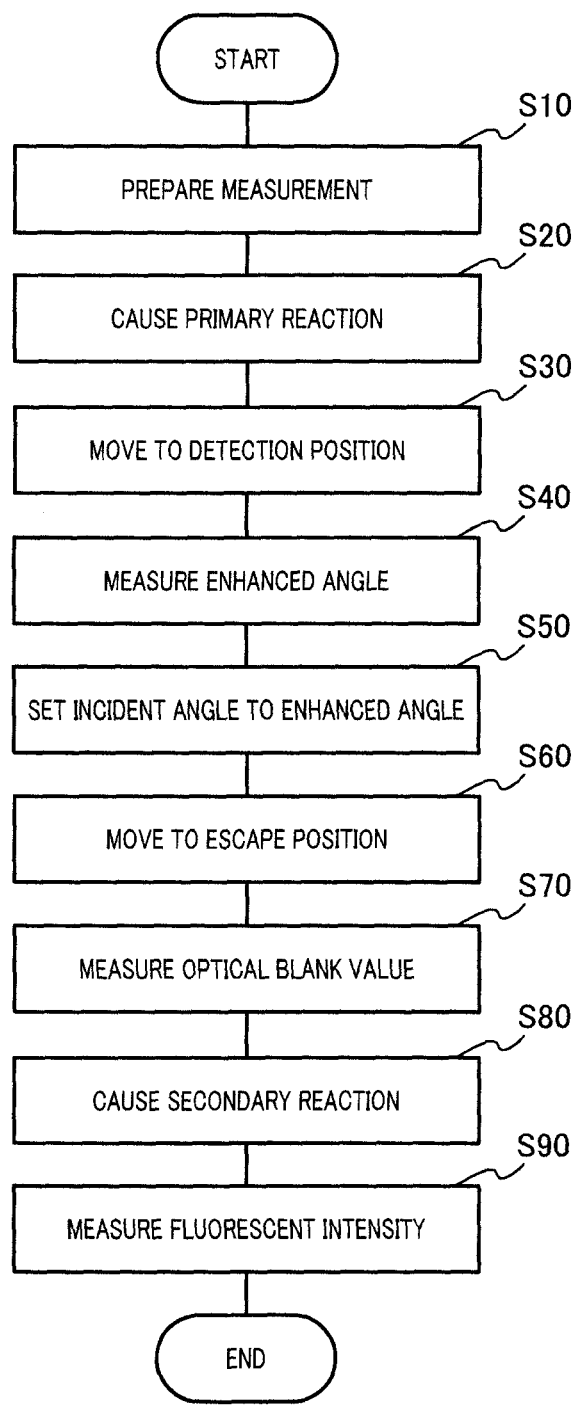
FIG. 2 is a flowchart illustrating an exemplary operation procedure of the SPFS device according to Embodiment 1.
Figure 3A:
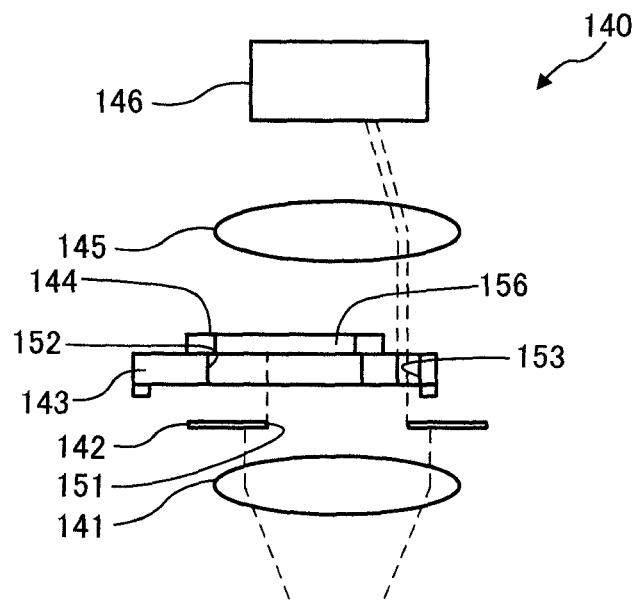
FIGS. 3A and 3B are diagrams for describing detection of plasmon scattering light and detection of fluorescence in the SPFS device according to Embodiment 1.
Figure 3B:
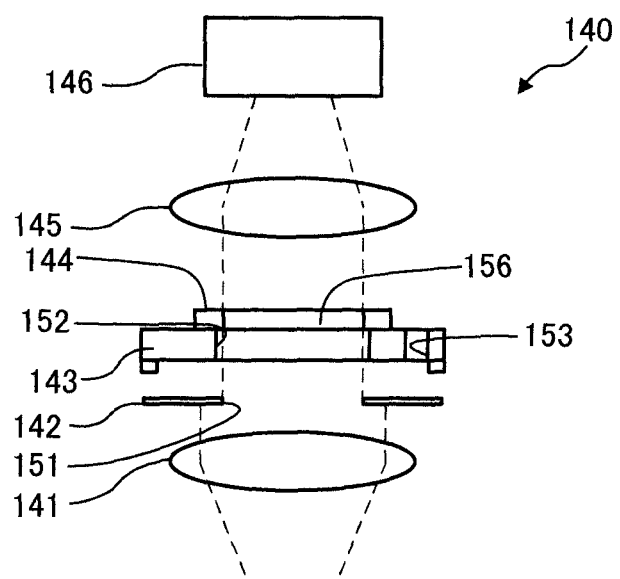

Next, the detection operation of SPFS device 100 will be described. FIG. 2 is a flowchart illustrating an exemplary operation procedure of SPFS device 100. FIGS. 3A and 3B are diagrams for describing detection of plasmon scattering light and detection of fluorescence. FIG. 3A is a diagram for describing detection of plasmon scattering light and FIG. 3B is a diagram for describing detection of fluorescence.

First, preparation for measurement is made (step S10). More specifically, analysis chip 10 is installed at a predetermined position of SPFS device 100. When a moisturizer is present in channel 41 of analysis chip 10, the inside of channel 41 is washed to remove the moisturizer so that the capturing body can appropriately capture the detection target substance.

Next, the detection target substance in the sample and the capturing body are made to react with each other (primary reaction, step S20). More specifically, the sample is injected into channel 41, and the sample and the capturing body are brought into contact with each other. When the detection target substance is present in the sample, at least some of the detection target substance is captured by the capturing body. Thereafter, the inside of channel 41 is washed with buffer solution or the like to remove a substance which has not been captured by the capturing body. The sample is not limited to a particular kind. Examples of the sample include bodily fluids such as blood, serum, plasma, urine, nasal mucus, saliva, and semen, and their diluted solutions.

Next, as illustrated in FIG. 3A, control processing section 164 moves filter holder 143 and places scattering-light transmitting section 153 on the light path in light-reception optical system unit 140 (step S30). While irradiating a predetermined position of metal film 30 (film-formation surface 22) with excitation light α, the incident angle of excitation light α with respect to metal film 30 (film-formation surface 22) is scanned to determine an optimum incident angle (step S40). Control processing section 164 controls light source unit 121 and angle adjusting section 122 to scan the incident angle of excitation light α with respect to metal film 30 (film-formation surface 22) while irradiating a predetermined position of metal film 30 (film-formation surface 22) with excitation light α. In addition, control processing section 164 controls light-sensor control section 162 such that light sensor 146 detects plasmon scattering light β from metal film 30 (the surface of metal film 30 and the vicinity of the surface). The plasmon scattering light β from metal film (the surface of metal film 30 and the vicinity of the surface) is collimated by first lens 141 and reaches light sensor 146 via scattering-light transmitting section 153. Thus, control processing section 164 obtains data containing the relationship between the incident angle of excitation light α and the intensity of plasmon scattering light β. Control processing section 164 analyzes the data and determines the incident angle (enhanced angle) at which the intensity of plasmon scattering light β is maximized Note that, the enhanced angle is basically determined based on the material and the shape of dielectric 20, the thickness of metal film 30, the refractive index of the liquid in channel 41 and/or the like, but the enhanced angle slightly varies depending on various factors such as the kind and the amount of fluorescent material in channel 41, and a shaping error of dielectric 20. In view of this, it is preferable to determine the enhanced angle each time analysis is performed. The enhanced angle is determined in the order of about 0.1 degrees.

Next, the incident angle of excitation light α with respect to metal film 30 (film-formation surface 22) is set to the enhanced angle determined at the previous step (step S50). More specifically, control processing section 164 controls angle adjusting section 122 to set the incident angle of excitation light α with respect to metal film 30 (film-formation surface 22) to the enhanced angle. In the following steps, the incident angle of excitation light α with respect to metal film 30 (film-formation surface 22) is kept at the enhanced angle.

Next, as illustrated in FIG. 3B, control processing section 164 moves filter folder 143 and disposes fluorescent transmitting region 156 in the light path of light-reception optical system unit 140 and also disposes scattering-light transmitting section 153 outside of the light path in light-reception optical system unit 140 (step S60). Furthermore, metal film 30 (film-formation surface 22) is irradiated with excitation light α, and the intensity of light having the same wavelength as fluorescence γ (optical blank value) is measured (step S70). More specifically, control processing section 164 controls light-source control section 161 to emit excitation light α to light source unit 121. Simultaneously, control processing section 164 controls first light-sensor control section 162 such that light sensor 146 detects the intensity of light having the same wavelength as fluorescence γ. At this time, excitation-light cut filter 144 does not allow plasmon scattering light β to pass through. Thus, light sensor 146 can measure the intensity of light that becomes a noise to be precise (optical blank value). The measurement value is sent to control processing section 164 and recorded as an optical blank value.

Next, the detection target substance that has been captured by the capturing body is labeled by a fluorescent material (secondary reaction, step S80). More specifically, a fluorescent labeling solution is injected into channel 41. The fluorescence labeling solution is, for example, a buffer solution containing an antibody (secondary antibody) labeled by a fluorescent material. When the fluorescent labeling solution is injected into channel 41, the fluorescent labeling solution makes contact with the detection target substance, and the detection target substance is labeled by the fluorescent material. Thereafter, the inside of channel 41 is washed with buffer solution and/or the like to remove a free fluorescent material and/or the like.

Finally, metal film 30 (film-formation surface 22) is irradiated with excitation light α and the intensity of fluorescence γ emitted from metal film 30 (the surface of metal film 30 and the vicinity of the surface) is measured (step S90). To be more specific, control processing section 164 controls light-source control section 161 to emit excitation light α to light source unit 121. Simultaneously, control processing section 164 controls light-sensor control section 162 such that light sensor 146 detects fluorescence γ emitted from metal film 30 (metal film 30 and the vicinity of metal film 30). At this time, since excitation-light cut filter 144 does not allow plasmon scattering light β to pass therethrough, only fluorescence γ is detected by light sensor 146. Control processing section 164 subtracts the optical blank value from the measurement value to calculate a fluorescent intensity correlated with the amount of the detection target substance. The fluorescent intensity is converted to the amount or the concentration of the detection target substance and/or the like as necessary.

Through the above-mentioned procedure, since scattering-light transmitting section 153 for detecting plasmon scattering light β is disposed at filter folder 143 in the vicinity of the excitation-light cut filter having fluorescent transmitting region 156 for detecting fluorescence γ, the presence or amount of the detection target substance in the sample can be detected without significantly moving excitation-light cut filter 144.

As described above, in SPFS device 100 according to the present embodiment, it is not necessary to significantly move excitation-light cut filter 144 from the light path of light-reception optical system unit 140 even when an optimum incident angle (enhanced angle) of excitation light α with respect to metal film 30 (film-formation surface 22) is determined. Accordingly, SPFS device 100 according to the present embodiment does not require complete removal of the excitation-light cut filter from the fluorescent light path unlike the SPFS device according to the related art (see PTL 2), thus enabling downsizing. Moreover, SPFS device 100 according to the present embodiment can detect the presence or amount of the detection target substance with high sensitivity and accuracy.

Embodiment 2

As with SPFS device 100 according to Embodiment 1, an SPFS device according to Embodiment 2 includes chip holder 12, excitation optical system unit 120, light-reception optical system unit 240 and control section 160. The SPFS device according to Embodiment 2 is different from SPFS device 100 according to Embodiment 1 only in the configuration of light-reception optical system unit 240. Therefore, in the present embodiment, only light-reception optical system unit 240 is described.

Figure 4A:
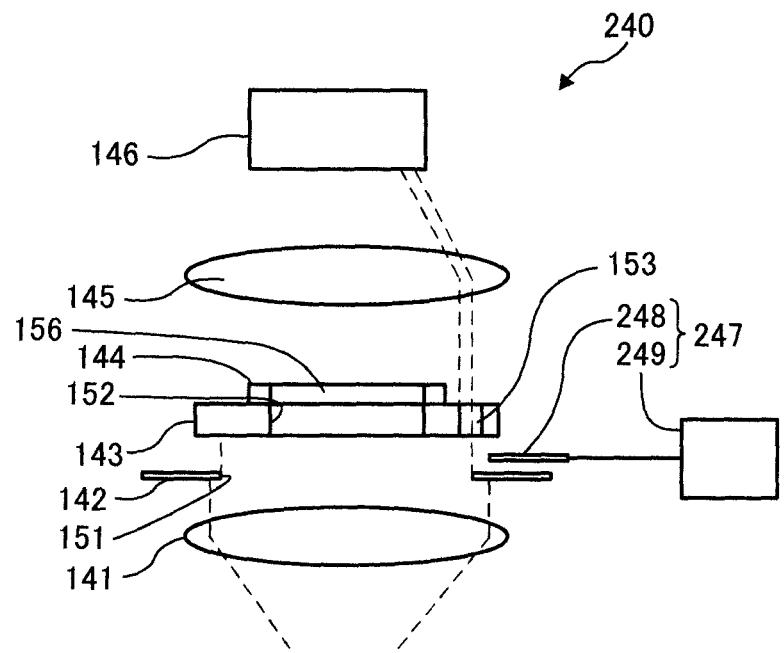
FIGS. 4A and 4B are diagrams for describing detection of plasmon scattering light and detection of fluorescence in an SPFS device according to Embodiment 2.
Figure 4B:
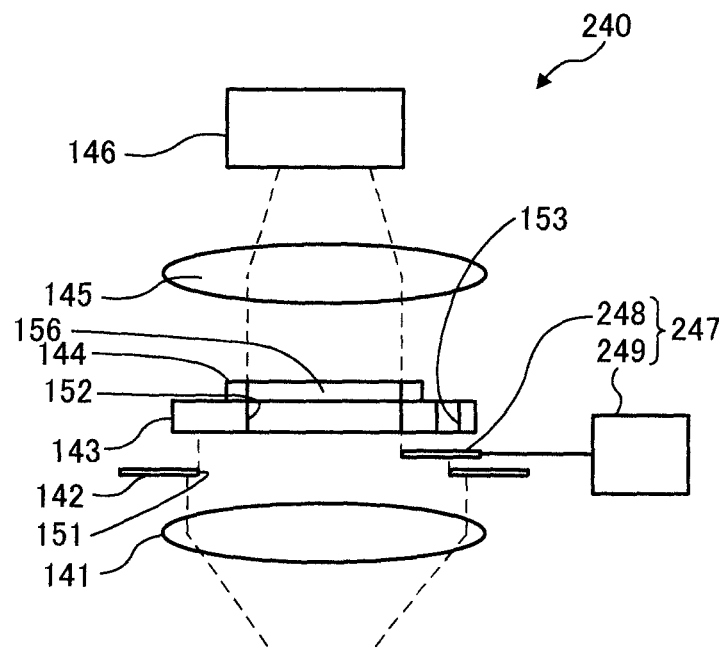

FIGS. 4A and 4B are diagrams for describing detection of plasmon scattering light β and detection of fluorescence γ in the SPFS device according to Embodiment 2. FIG. 4A is a diagram for describing detection of plasmon scattering light β, and FIG. 4B is a diagram for describing detection of fluorescence γ.

As illustrated in FIGS. 4A and 4B, light-reception optical system unit 240 includes first lens 141, diaphragm 142, filter holder 143, excitation-light cut filter 144, second lens 145, light sensor 146, and transmission adjusting section 247. First lens 141, diaphragm 142, filter holder 143, excitation-light cut filter 144, second lens 145, and light sensor 146 in light-reception optical system unit 240 are identical to the respective components of light-reception optical system unit 140 according to Embodiment 1.

Transmission adjusting section 247 blocks plasmon scattering light β heading to scattering-light transmitting section 153. Transmission adjusting section 147 is an electromagnetic shutter or liquid-crystal shutter. In this embodiment, transmission adjusting section 247 is an electromagnetic shutter. Electromagnetic shutter (transmission adjusting section) 247 includes shutter body 248 and power supply 249 for putting shutter body 248 into a transparent state and block state. The term "transparent state" used herein means a state in which at least some of scattering-light transmitting section 153 is opened and plasmon scattering light β can pass through scattering-light transmitting section 153 (see FIG. 4A). In addition, the term "block state" means a state in which shutter body 248 covers the entirety of scattering-light transmitting section 153, so that plasmon scattering light β cannot pass through scattering-light transmitting section 153 (see FIG. 4B). As described above, putting scattering-light transmitting section 153 into the transparent state or block state by transmission adjusting section 247 makes it possible to easily switch between detection of plasmon scattering light β and detection of fluorescence γ.

Figure 5:
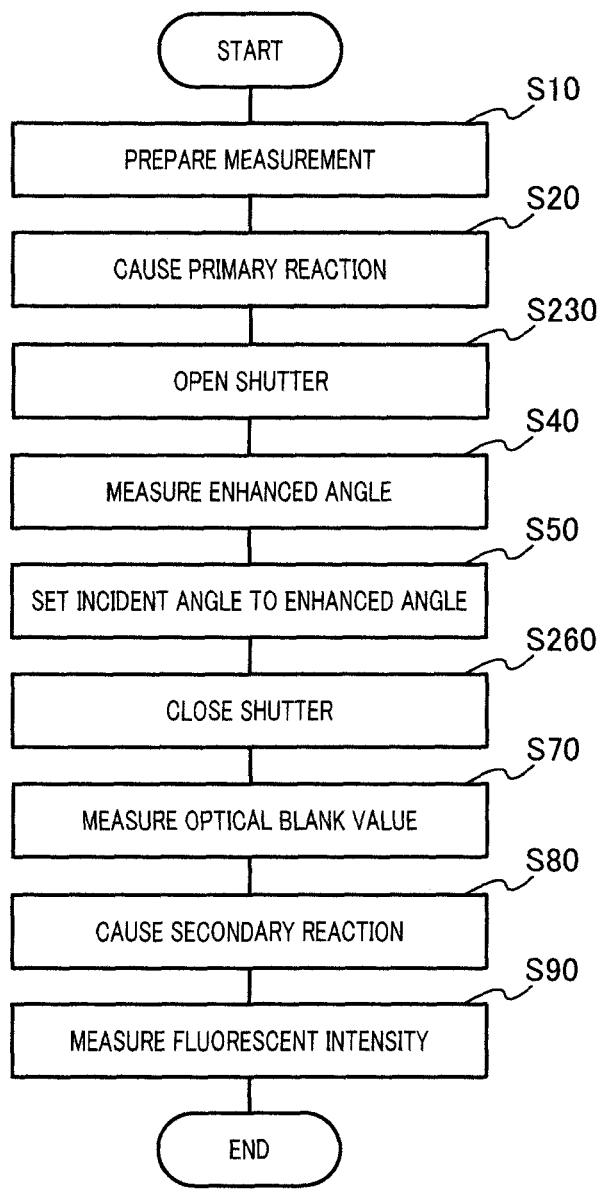
FIG. 5 is a flowchart illustrating an exemplary operation procedure of the SPFS device according to Embodiment 2.

Next, the detection operation of the SPFS device according to Embodiment 2 will be described. FIG. 5 is a flowchart illustrating an exemplary operation procedure of the SPFS device.

First, preparation for measurement is made (step S10). Next, the detection target substance in the sample and the capturing body are made to react with each other (primary reaction, step S20).

Next, as illustrated in FIG. 4A, control processing section 164 opens electromagnetic shutter 247 and puts plasmon scattering light β into the transparent state (step S230). While irradiating a predetermined position of metal film 30 (film-formation surface 22) with excitation light α, the incident angle of excitation light α with respect to metal film 30 (film-formation surface 22) is scanned to determine an optimum incident angle (step S40).

Next, the incident angle of excitation light α with respect to metal film 30 (film-formation surface 22) is set to the enhanced angle determined at the previous step (step S50). In the following steps, the incident angle of excitation light α with respect to metal film 30 (film-formation surface 22) is kept at the enhanced angle.

Next, as illustrated in 4B, control processing section 164 closes electromagnetic shutter 247 to set the block state with respect to plasmon scattering light β (step S260). Metal film 30 (film-formation surface 22) is irradiated with excitation light α, and the intensity of light having the same wavelength as fluorescence γ (optical blank value) is measured (step S70).

Next, the detection target substance that has been captured by the capturing body is labeled by a fluorescent material (secondary reaction, step S80). Finally, metal film 30 (film-formation surface 22) is irradiated with excitation light α, and the intensity of fluorescence γ emitted from metal film 30 (the surface of metal film 30 and the vicinity of the surface) is measured (step S90).

Through the above-mentioned procedure, it is possible to detect the presence or amount of the detection target substance in the sample without moving excitation-light cut filter 144.

As described above, in the SPFS device according to the present embodiment, it is not necessary to move excitation-light cut filter 144 from the light path of light-reception optical system unit 240. Accordingly, the SPFS device according to the present embodiment does not require moving of the excitation-light cut filter in the horizontal direction unlike the SPFS device according to the related art (see PTL 2), thus enabling downsizing. In addition, the presence or amount of the detection target substance can be detected with high sensitivity and accuracy.

Embodiment 3

As with SPFS device 100 according to Embodiment 1 and the SPFS device according to Embodiment 2, an SPFS device according to Embodiment 3 includes chip holder 12, excitation optical system unit 120, light-reception optical system unit 340 and control section 160. The SPFS device according to Embodiment 3 is different from SPFS device 100 according to Embodiment 1 and the SPFS device according to Embodiment 2 only in the configuration of light-reception optical system unit 340. Therefore, in the present embodiment, only light-reception optical system unit 340 is described.

Figure 6A:
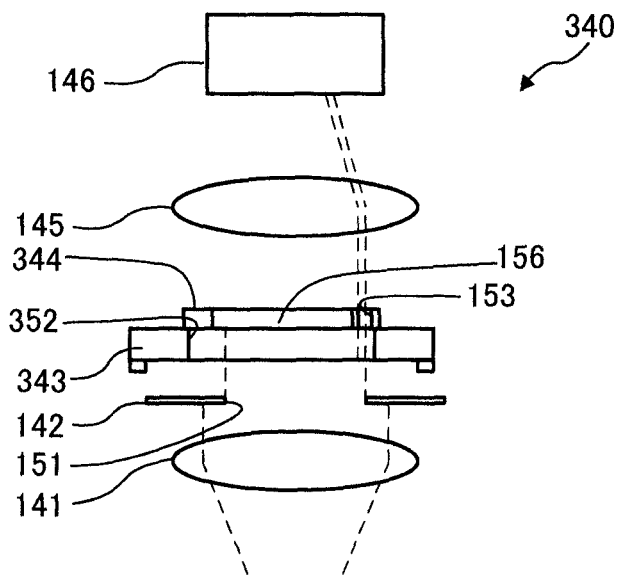
FIGS. 6A and 6B are diagrams for describing detection of plasmon scattering light and detection of fluorescence in an SPFS device according to Embodiment 3.
Figure 6B:
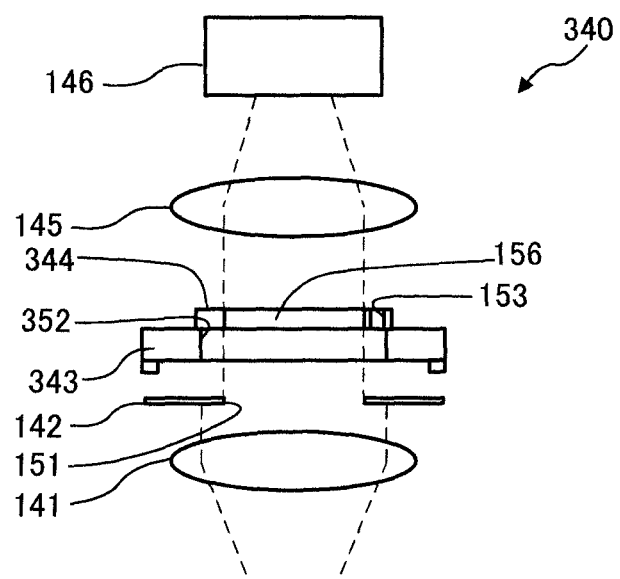

FIGS. 6A and 6B are diagrams for describing detection of plasmon scattering light β and detection of fluorescence γ. FIG. 6A is a diagram for describing detection of plasmon scattering light β, and FIG. 6B is a diagram for describing detection of fluorescence γ.

As illustrated in FIGS. 6A and 6B, light-reception optical system unit 340 includes first lens 141, diaphragm 142, filter holder 343, excitation-light cut filter 344, second lens 145, light sensor 146, and transmission adjusting section 147. First lens 141, diaphragm 142, second lens 145, and light sensor 146 in light-reception optical system unit 340 according to Embodiment 3 are identical to the respective components of light-reception optical system unit 140 according to Embodiment 1.

In Embodiment 3, filter holder 343 includes third through-hole 352. Third through-hole 352 is disposed at a center portion of filter holder 343. In other words, in Embodiment 3, only one through-hole is formed in filter holder 343. Third through-hole 352 is formed larger in size than first through-hole 152 formed in filter folder 143 according to Embodiment 1. Accordingly, filter holder 343 according to Embodiment 3 holds excitation-light cut filter 344 at an outer edge portion, compared with filter holder 143 according to Embodiment 1.

Excitation-light cut filter 344 includes fluorescent transmitting region 156 which allows fluorescence γ to pass through, and scattering-light transmitting section 153 which allows plasmon scattering light β to pass through. Scattering-light transmitting section 153 is disposed so as to avoid fluorescent transmitting region 156. As described above, a transparent substrate whose one or both surfaces are coated with a dielectric multilayer film may be used for excitation-light cut filter 344, for example. Accordingly, scattering-light transmitting section 153 can be easily formed by previously applying masking to the region where scattering-light transmitting section 153 is to be formed, then forming a dielectric multilayer film, and lastly peeling off the masking. It is preferable that the area of scattering-light transmitting section 153 be not greater than 1/1000 of the area of fluorescent transmitting region 156 when viewed in a plan view.

Next, the detection operation of the SPFS device according to Embodiment 3 will be described. No that, the flowchart for this operation is the same as that of SPFS device 100 according to Embodiment 1, so that the flowchart is omitted herein.

First, preparation for measurement is made (step S10). Next, the detection target substance in the sample and the capturing body are made to react with each other (primary reaction, step S20). Next, as illustrated in FIG. 6A, control processing section 164 moves filter holder 343 and places scattering-light transmitting section 153 on the light path in light-reception optical system unit 340 (step S30). While irradiating a predetermined position of metal film 30 (film-formation surface 22) with excitation light α, the incident angle of excitation light α with respect to metal film 30 (film-formation surface 22) is scanned to determine an optimum incident angle (step S40). Next, the incident angle of excitation light α with respect to metal film 30 (film-formation surface 22) is set to the enhanced angle determined at the previous step (step S50). Next, as illustrated in FIG. 6B, control processing section 164 moves filter holder 343, disposes fluorescent transmitting region 156 in the light path of light-reception optical system unit 340 and also disposes scattering-light transmitting section 153 outside of the light path in light-reception optical system unit 340 (step S60). Furthermore, metal film 30 (film-formation surface 22) is irradiated with excitation light α, and the intensity of light having the same wavelength as fluorescence γ (optical blank value) is measured (step S70). Next, the detection target substance that has been captured by the capturing body is labeled by a fluorescent material (secondary reaction, step S80). Finally, metal film 30 (film-formation surface 22) is irradiated with excitation light α, and the intensity of fluorescence γ emitted from metal film 30 (the surface of metal film 30 and the vicinity of the surface) is measured (step S90).

Through the above-mentioned procedure, it is possible to detect the presence or amount of the detection target substance in the sample without significantly moving the excitation-light cut filter 344 as in SPFS device 100 according to Embodiment 1.

As described above, in the SPFS device according to the present embodiment, it is not necessary to significantly move excitation-light cut filter 144 from the light path of light-reception optical system unit even when an optimum incident angle (enhanced angle) of excitation light α with respect to metal film 30 (film-formation surface 22) is determined, as compared with SPFS device 100 according to Embodiment 1.

Note that, although not illustrated in particular, scattering-light transmitting section 153 may be disposed within fluorescent transmitting region 156 in excitation-light cut filter 344. In this case, it is preferable that the size of scattering-light transmitting section 153 be not greater than $\frac{1}{1000}$ of the size of fluorescent transmitting region 156. As described herein, scattering-light transmitting section 153 is so small in size compared with fluorescent transmitting region 156 that plasmon scattering light β does not interfere with detection of fluorescence γ. In addition, it is not necessary to move excitation-light cut filter 344 between detection of plasmon scattering light β and detection of fluorescence γ. Thus, the apparatus can be further downsized.

Embodiment 4

The SPFS device according to Embodiment 4 includes chip holder 12, excitation optical system unit 120, light-reception optical system unit 440, and control section 160 as in the SPFS device described above. The SPFS device according to Embodiment 4 is different from the SPFS device according to Embodiment 3 only in the configuration of light-reception optical system unit 440. Thus, a description of only light-reception optical system unit 440 will be given in this embodiment.

Figure 7A:
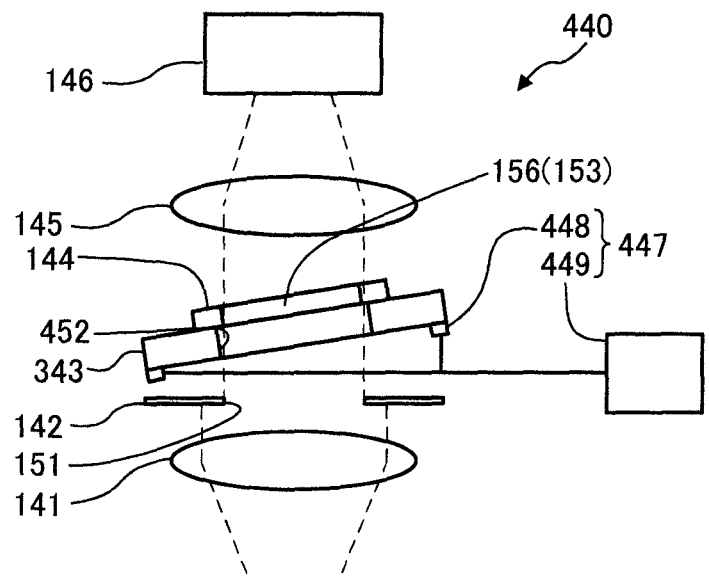
FIGS. 7A and 7B are diagrams for describing detection of plasmon scattering light and detection of fluorescence in an SPFS device according to Embodiment 4.
Figure 7B:
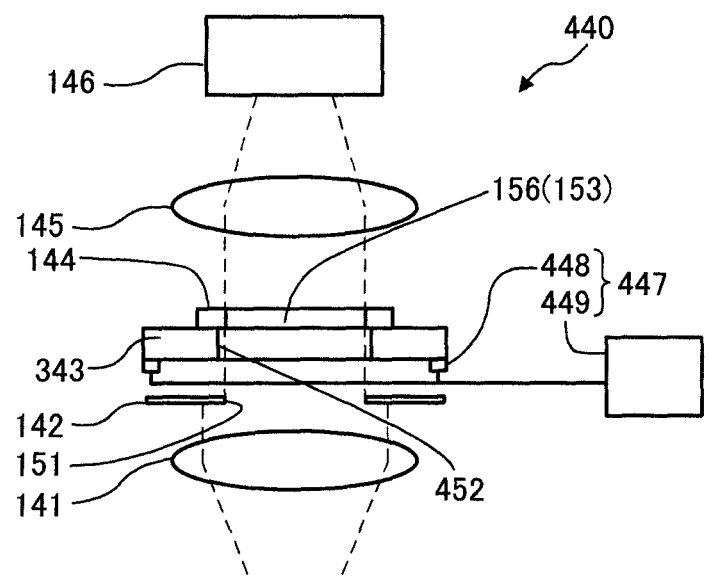

FIGS. 7A and 7B are diagrams for describing detection of plasmon scattering light β and detection of fluorescence γ in Embodiment 4. FIG. 7A is a diagram for describing detection of plasmon scattering light β and FIG. 7B is a diagram for describing detection of fluorescence γ.

As illustrated in FIGS. 7A and 7B, light-reception optical system unit 440 includes first lens 141, diaphragm 142, filter holder 143, excitation-light cut filter 144, second lens 145, light sensor 146, and transmission adjusting section 447. First lens 141, diaphragm 142, filter holder 343, second lens 145 and light sensor 146 in light-reception optical system unit 440 according to Embodiment 4 are identical to those elements in light-reception optical system unit 140 according to Embodiment 1.

In this embodiment, filter holder 343 includes fourth through-hole 452. Fourth through-hole 452 is formed at a center portion of filter holder 343 in a size substantially identical to the outer shape of excitation-light cut filter 144.

Transmission adjusting section 447 includes: θ stage 448 which can freely turn excitation-light cut filter 144 via filter holder 343 around a rotation axis in a direction orthogonal to the optical axis of fluorescence γ or plasmon scattering light β; and θ turn mechanism 449 for turning θ stage 448 by θ.

Figure 8:
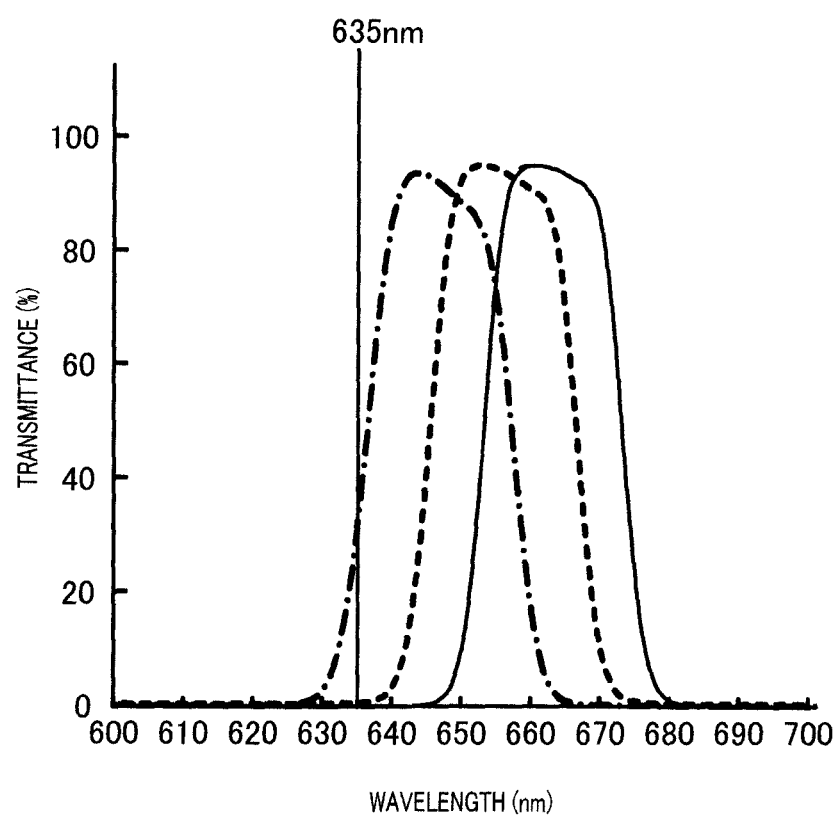
FIG. 8 is a graph indicating the relationship between the wavelength passing through an excitation-light cut filter and the transmittance.

Next, a description will be given of detection of plasmon scattering light β by turning excitation-light cut filter 144 around the turn axis by θ. FIG. 8 is a graph indicating the relationship between the wave length passing through excitation-light cut filter 144 and the transmittance of excitation-light cut filter 144. The solid line in FIG. 8 indicates a case where turning angle of excitation-light cut filter 144 is 0 degrees. The broken line in FIG. 8 indicates a case where the turning angle of excitation-light cut filter 144 is 15 degrees. The dashed-dotted line in FIG. 8 indicates a case where the turning angle of excitation-light cut filter 144 is 20 degrees. Excitation-light cut filter 144 having a transmission wavelength band within a range from 652 nm to 672 nm will be described as an example. Moreover, the wavelength of excitation light is set to 635 nm.

As illustrated in FIG. 8, it can be seen that, the wavelength of the light passing through excitation-light cut filter 144 shifts to the short wavelength side when excitation-light cut filter 144 having the multilayer film described above is tilted. In other words, tilting excitation-light cut filter 144 (multilayer film) allows plasmon scattering light β to pass through excitation-light cut filter 144. More specifically, as illustrated by the solid line in FIG. 8, it can be seen that, when the turning angle (incident angle) of excitation-light cut filter 144 is 0 degrees, excitation light α is sufficiently blocked. Meanwhile, as illustrated by the dashed-dotted line in FIG. 8, approximately 20% of the light having a wavelength of 635 nm passes through excitation-light cut filter 144 when the turning angle of excitation light cut filter 144 (incident angle) is 20 degrees. Accordingly, adjustment of the tilt angle of excitation-light cut filter 144 enables switching between detection of plasmon scattering light β and detection of fluorescence γ.

Figure 9:
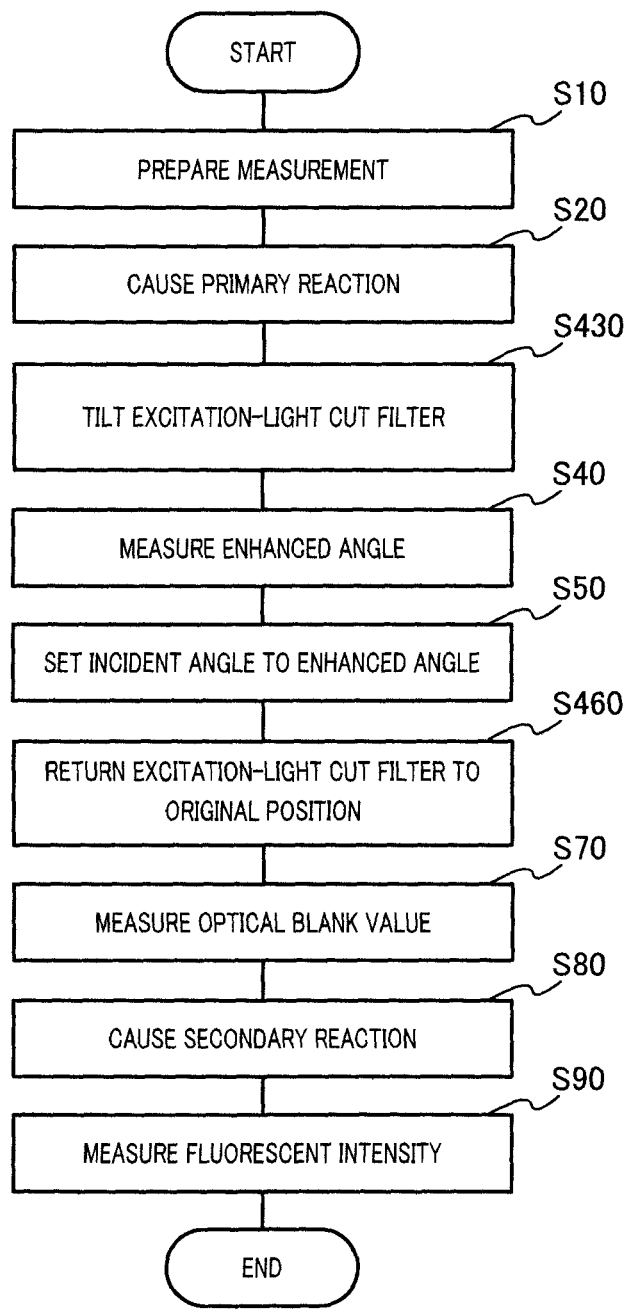
FIG. 9 is a flowchart illustrating an exemplary operation procedure of the SPFS device according to Embodiment 4.

Next, a description will be given of a detection operation of the SPFS device according to Embodiment 4. FIG. 9 is a flowchart illustrating an exemplary operation procedure of the SPFS device according to Embodiment 4.

First, preparation for measurement is made (step S10). Subsequently, a detection target substance in a sample and a capturing body are made to react with each other (primary reaction, step S20).

Next, as illustrated in FIG. 7A, control processing section 164 tilts excitation-light cut filter 144 (multilayer film) at a predetermined angle by turning filter holder 343 by θ (step S430). While a predetermined position of metal film 30 (film-formation surface 22) is irradiated with excitation light α, the incident angle of excitation light α for metal film 30 (film-formation surface 22) is scanned to determine an optimum incident angle (step S40).

Next, the incident angle of excitation light α with respect to metal film 30 (film-formation surface 22) is set to the enhanced angle determined at the previous step (step S50). In the following steps, the incident angle of excitation light α with respect to metal film 30 (film-formation surface 22) is kept at the enhanced angle.

Next, as illustrated in FIG. 7B, control processing section 164 puts excitation-light cut filter 144 back to the original position before the tilting by turning filter holder 343 by θ in the reverse direction (step S460). Metal film 30 (film-formation surface 22) is irradiated with excitation light α to measure the intensity of light (optical blank value) having the same wavelength as fluorescence γ (step S70).

Next, the detection target substance that has been captured by the capturing body is labeled by a fluorescent material (secondary reaction, step S80). Finally, metal film 30 (film-formation surface 22) is irradiated with excitation light α and the intensity of fluorescence γ emitted from metal film 30 (the surface of metal film 30 and the vicinity of the surface) is measured (step S90).

Through the above-mentioned procedure, it is possible to detect the presence or amount of a detection target substance in a sample without moving the excitation-light cut filter 144 in a planner direction.

As described above, the SPFS device according to the present embodiment brings about the effects similar to those brought about by the SPFS device according to Embodiment 2.

This application is entitled to and claims the benefit of Japanese Patent Application No. 2014-020356 filed on Feb.

5, 2014, the disclosure of which including the specification, drawings and abstract is incorporated herein by reference in its entirety.

INDUSTRIAL APPLICABILITY

The surface plasmon resonance fluorescence analysis device and the surface plasmon resonance fluorescence analysis method according to the present invention can measure a detection target substance with high reliability, and therefore are suitable for laboratory tests and the like, for example.

REFERENCE SIGNS LIST

10 Analysis chip
12 Chip holder
20 Dielectric
21 Incidence surface
22 Film-formation surface
23 Emission surface
30 Metal film
40 Channel closure
41 Channel
100 Surface plasmon resonance fluorescence analysis device (SPFS device)
120 Excitation optical system unit
121 Light source unit
122 Angle adjusting section
140, 240, 340, 440 Light-reception optical system unit
141 First lens
142 Diaphragm
143, 343 Filter holder
144, 344 Excitation-light cut filter
145 Second lens
146 Light sensor
147, 247, 447 Transmission adjusting section
151 Throttle hole
152 First through-hole
153 Second through-hole (scattering-light transmission section)
154, 448 Stage
155 Motor
156 Fluorescent transmitting region
160 Control section
161 Light-source control section
162 Light-sensor control section
163 Motor control section
164 Control processing section
248 Shutter body
249 Power supply
352 Third through-hole
449 Turn mechanism
452 Fourth through-hole

The invention claimed is:

1. A surface plasmon resonance fluorescence analysis device to which an analysis chip including a dielectric having a metal film on one surface of the dielectric is attached and in which the metal film is irradiated with excitation light through the dielectric to excite a fluorescent material for labelling a detection target substance on the metal film, and then fluorescence emitted from the fluorescent material is detected to thereby detect the presence or amount of the detection target substance, the surface plasmon resonance fluorescence analysis device comprising:
a chip holder configured to detachably hold the analysis chip;
an adjustable light source configured to emit excitation light to irradiate the metal film with the excitation light through the dielectric at an incident angle with respect to the metal film;
a light sensor configured to detect light emitted from the vicinity of a surface of the metal film, the surface facing away from the dielectric;
a filter holder between the metal film and the sensor, the filter holder configured to hold the excitation-light cut filter;
an excitation-light cut filter including a fluorescent transmitting region defined by a hole defined by the filter holder that allows fluorescence emitted from the metal film to pass through the region and blocks at least light having a certain wavelength of the excitation light, through which light emitted by the metal film passes, wherein a plan-view shape of the hole is the same as the plan-view shape of the fluorescent transmitting region; and
a scattering-light transmitting hole disposed at the excitation-light cut filter or the filter holder and configured to allow passage of plasmon scattering light emitted from the metal film;
a movable stage coupled to the filter holder to adjust the position of the filter holder to position the scattering light transmitting hole to allow the plasmon scattering light to pass through via the scattering-light-transmitting hole,
wherein a total area of the scattering-light transmitting hole in a plan view is smaller than a total area of the fluorescent transmitting region of the excitation-light cut filter in a plan view, and
the light sensor is further configured to detect fluorescence emitted from the metal film, the detected fluorescence being indicative of the presence or the amount of the detection target substance.

2. The surface plasmon resonance fluorescence analysis device according to claim 1, further comprising a at least one processing device configured to control the adjustable light source and the movable stage, wherein:
the at least one processing device allows the plasmon scattering light to pass through via the scattering-light transmitting hole by control of the movable stage, and
the at least one processing device controls the incident angle of the excitation light with respect to the metal film by the adjustable light source based on detection of the plasmon scattering light by the light sensor.

3. The surface plasmon resonance fluorescence analysis device according to claim 1, wherein the the movable stage causes movement of the scattering-light transmitting hole into a light path between the metal film and the light sensor when the light sensor detects the plasmon scattering light, and the the movable stage causes movement of the scattering-light transmitting hole to outside of the light path when the light sensor detects the fluorescence.

4. The surface plasmon resonance fluorescence analysis device according to claim 1, wherein an area of the scattering-light transmitting hole in a plan view is not greater than $\frac{1}{1000}$ of an area of the fluorescent transmitting region in a plan view.

5. A surface plasmon resonance fluorescence analysis device to which an analysis chip including a dielectric having a metal film on one surface of the dielectric is attached and in which the metal film is irradiated with excitation light through the dielectric to excite a fluorescent material for labelling a detection target substance on the metal film, and then fluorescence emitted from the fluorescent material is detected to thereby detect the presence or amount of the detection target substance, the surface plasmon resonance fluorescence analysis device comprising:
- a chip holder configured to detachably hold the analysis chip;
- an adjustable light source configured to emit excitation light at a variable incident angle with respect to the metal film to irradiate the metal film with the excitation light through the dielectric at a predetermined incident angle;
- a light sensor configured to detect light emitted from the vicinity of a surface of the metal film, the surface facing away from the dielectric;
- an excitation-light cut filter including a fluorescent transmitting region defined by a hole by the excitation-light cut filter that allows fluorescence emitted from the metal film to pass through the region and blocks at least light having a certain wavelength of the excitation light, the fluorescent transmitting region being defined by a hole defined upstream of the excitation-light cut filter, through which light emitted by the metal film passes, wherein a plan-view shape of the hole is the same as the plan-view shape of the fluorescent transmitting region;
- a filter holder between the metal film and the sensor, the filter holder being configured to hold the excitation-light cut filter;
- a scattering-light transmitting hole disposed at the excitation-light cut filter or the filter holder and configured to allow passage of plasmon scattering light emitted from the metal film; and
- a shutter to selectively block plasmon scattering light heading to the scattering-light transmitting hole;
- wherein a total area of the scattering-light transmitting hole in a plan view is smaller than a total area of the fluorescent transmitting region of the excitation-light cut filter in a plan view, and
- the light sensor is further configured to detect fluorescence emitted from the metal film, the detected fluorescence being indicative of the presence or the amount of the detection target substance.

6. The surface plasmon resonance fluorescence analysis device according to claim 5, wherein the shutter comprises a liquid crystal shutter.

7. The surface plasmon resonance fluorescence analysis device according to claim 1, wherein the scattering-light transmitting hole is disposed at the filter holder.

8. The surface plasmon resonance fluorescence analysis device according to claim 1, wherein the scattering-light transmitting hole is disposed at the excitation-light cut filter so as to avoid the fluorescent transmitting region.

9. The surface plasmon resonance fluorescence analysis device according to claim 1, wherein the scattering-light transmitting hole is disposed within the fluorescent transmitting region of the excitation-light cut filter and an area of the fluorescent transmitting region is no bigger than an area of the excitation-light cut filter.

10. The surface plasmon resonance fluorescence analysis device according to claim 1, further comprising:
- at least one lens between the metal film and the scattering-light transmitting hole, the at least one lens to direct light from the metal film the scattering-light transmitting hole along an optical axis,
- wherein the scattering-light transmitting hole has a center axis disposed along the optical axis.

11. A surface plasmon resonance fluorescence analysis method in which fluorescence that is emitted by a fluorescent material for labelling a detection target substance when the fluorescent material is excited by localized-field light on a basis of surface plasmon resonance is detected to thereby detect the presence or amount of the detection target substance, the surface plasmon resonance fluorescence analysis method comprising:
- disposing the detection target substance on a metal film disposed on one surface of a dielectric;
- scanning an incident excitation light with respect to the metal film through a plurality of angles;
- while scanning the incident excitation light, irradiating the metal film with excitation light through the dielectric while a scattering-light transmitting hole is in a position where the plasmon scattering light is allowed to pass through the scattering-light transmitting hole,
- wherein the scattering-light transmitting hole is formed at a filter holder or at an excitation light cut filter which includes a fluorescent transmitting region that allows fluorescence to pass through the region and blocks at least light having a certain wavelength of excitation light, the fluorescent transmitting region being defined by a second hole defined by the filter holder;
- detecting the intensity of the plasmon scattering light that has been emitted from the metal film and has passed through the scattering-light transmitting hole while the metal film is irradiated with excitation light through the dielectric at the plurality of angles;
- determining an enhanced angle that is an incident angle at which intensity of plasmon scattering light is maximized, based on the intensity of the detected plasmon scattering light;
- irradiating the metal film with the excitation light through the dielectric at the enhanced angle; and
- detecting the intensity of the fluorescence that has been emitted from the fluorescent materials at the enhanced angle, wherein the detected intensity of the fluorescence is indicative of the presence or amount of the detection target substance;
- wherein a total area of the scattering-light transmitting hole in a plan view is smaller than a total area of the fluorescent transmitting region of the excitation-light cut filter in a plan view.

12. The surface plasmon resonance fluorescence analysis device according to claim 1, wherein the scattering-light transmitting hole is disposed at a distance from an end portion of the fluorescent transmitting region that is shorter than a diameter of the fluorescent transmitting region.

13. The surface plasmon resonance fluorescence analysis method according to claim 11, further comprising:
- moving the excitation-light cut filter or the filter holder by a distance shorter than a diameter of the fluorescent transmitting region to dispose the fluorescent transmitting region in the position where the fluorescence is allowed to pass through the region.

14. The surface plasmon resonance fluorescence analysis device according to claim 1, further comprising a diaphragm upstream of the excitation-light filter, wherein the fluorescent scattering-light hole is defined by the diaphragm.

15. The surface plasmon resonance fluorescence analysis device according to claim 1, wherein the scattering-light transmitting hole is defined by the filter holder.

16. The surface plasmon resonance fluorescence analysis device according to claim 5, wherein the shutter comprises an electromagnetic shutter.

* * * * *